United States Patent
Zimmerman et al.

(10) Patent No.: US 11,311,475 B2
(45) Date of Patent: Apr. 26, 2022

(54) SKIN CARE COMPOSITIONS CONTAINING PEPTIDE COMPOUND AND APHANOTHECE SACRUM EXOPOLYSACCHARIDE EXTRACT

(71) Applicant: The Procter & Gamble Company, Cincinnati, OH (US)

(72) Inventors: Dean Arthur Zimmerman, Liberty Township, OH (US); Peter Brendan Styczynski, West Chester, OH (US)

(73) Assignee: The Procter and Gamble Company, Cincinnati, OH (US)

(*) Notice: Subject to any disclaimer, the term of this patent is extended or adjusted under 35 U.S.C. 154(b) by 0 days.

(21) Appl. No.: 16/721,409

(22) Filed: Dec. 19, 2019

(65) Prior Publication Data

US 2020/0206124 A1    Jul. 2, 2020

Related U.S. Application Data

(60) Provisional application No. 62/787,706, filed on Jan. 2, 2019.

(51) Int. Cl.
| | | |
|---|---|---|
| *A61K 8/9717* | (2017.01) | |
| *A61K 8/64* | (2006.01) | |
| *A61K 8/73* | (2006.01) | |
| *A61Q 19/08* | (2006.01) | |

(52) U.S. Cl.
CPC .............. *A61K 8/9717* (2017.08); *A61K 8/64* (2013.01); *A61K 8/73* (2013.01); *A61Q 19/08* (2013.01)

(58) Field of Classification Search
CPC ......................................................... A61K 8/64
See application file for complete search history.

(56) References Cited

U.S. PATENT DOCUMENTS

| | | |
|---|---|---|
| 6,492,326 B1 | 12/2002 | Robinson |
| 6,620,419 B1 | 9/2003 | Lintner |
| 8,044,028 B2 | 10/2011 | Moussou et al. |
| 8,568,751 B1 | 10/2013 | Goldsberry et al. |
| 8,871,717 B2 | 10/2014 | Osborne |
| 9,511,010 B2 | 12/2016 | Van Den Nest |
| 9,616,011 B2 | 4/2017 | Osborne |
| 10,265,348 B2 | 4/2019 | Soley Astals et al. |
| 2011/0229538 A1* | 9/2011 | Matravers ............ A61K 8/9711 424/401 |
| 2011/0300199 A1 | 12/2011 | Garcia et al. |
| 2012/0121675 A1 | 5/2012 | Garcia et al. |
| 2013/0017239 A1 | 1/2013 | Viladot et al. |
| 2013/0064876 A1 | 3/2013 | Viladot et al. |
| 2013/0101662 A1 | 4/2013 | Carreno et al. |
| 2013/0216596 A1 | 8/2013 | Viladot et al. |
| 2013/0302261 A1 | 11/2013 | Courtois et al. |
| 2015/0071974 A1 | 3/2015 | Ferrer Montiel et al. |
| 2015/0098989 A1 | 4/2015 | Ferrer Montiel et al. |
| 2015/0140046 A1 | 5/2015 | Ferrer Montiel et al. |
| 2015/0183823 A1 | 7/2015 | Garca et al. |
| 2016/0213599 A1* | 7/2016 | Devie |
| 2017/0296458 A1* | 10/2017 | Osorio |
| 2017/0319462 A1 | 11/2017 | Marchant et al. |
| 2018/0303749 A1* | 10/2018 | Annalisa |
| 2018/0344623 A1* | 12/2018 | Valerie |
| 2018/0369579 A1 | 12/2018 | Jang et al. |
| 2019/0336429 A1 | 11/2019 | Chavan et al. |

FOREIGN PATENT DOCUMENTS

| | | | |
|---|---|---|---|
| CN | 105147534 A | | 12/2015 |
| CN | 107260626 A | * | 10/2017 |
| CN | 107260626 A | | 10/2017 |
| CN | 109330964 A | | 2/2019 |
| CN | 110302089 A | | 10/2019 |
| CN | 110585056 A | | 12/2019 |
| KR | 20100061089 A | | 6/2010 |
| KR | 101072027 B1 | | 10/2011 |
| WO | 2017079248 A | | 5/2017 |
| WO | 2019079291 A1 | | 4/2019 |
| WO | 2019173782 A1 | | 9/2019 |

OTHER PUBLICATIONS

Doi (Topical treatment with sacran, a sulfated polysaccharide from *Aphanothece sacrum*, improves corneocyte-derived parameters, Journal of Dermatology 2017; 44:1360-1367) (Year: 2017).*
Schagen (Topical Peptide Treatments with Effective Anti-Aging Results, Cosmetics Review MDPI, May 22, 2017) (Year: 2017).*
CN-107260626-A, translated claims, Ligang (Year: 2017).*
CN-107260626-A, translated description, Ligang (Year: 2017).*
"All in One Jewelry Cream", Retrieved from: www.gnpd.com, Sep. 2015, 7 Pages.
"In Seven Exceed Limit DG Serum", Retrieved from: www.gnpd.com, Dec. 2016, 6 Pages.
"Perfect Lift Gel", Retrieved from: www.gnpd.com. Mar. 2016, 5 Pages.
"Sacran", Retrieved from: http://web.archive.org/web/20150927070005/http/www.daitokasei.com/news/img/SACRAN.pdf, Jan. 2011, 8 Pages.
"Sacran", Retrieved from: https://www.kokenmpc.co.jp/english/products/cosmetic_materials/sacran/index.html, Jan. 2005, 4 Pages.
PCT Search Report and Written Opinion for PCT/US2019/067035 dated Apr. 2, 2020.
Motoyama, et al., "Potential use of a megamolecular polysaccharide sacran as a hydrogel-based sustained release system", In Journal of Chemical and Pharmaceutical Bulletin, vol. 62, No. 7, Apr. 16. 2014, pp. 636-641.
Schagen, Silke Karin, "Topical Peptide Treatments with Effective Anti-Aging Results", Cosmetics, vol. 4, No. 2, May 22, 2017, 14 Pages.

* cited by examiner

*Primary Examiner* — Terry A McKelvey
*Assistant Examiner* — Jacob A Boeckelman
(74) *Attorney, Agent, or Firm* — Alexandra S. Anoff

(57) ABSTRACT

Skin care compositions comprising *Aphanothece sacrum* exopolysaccharide extract help the skin penetration of peptide compounds contained therein.

17 Claims, No Drawings

Specification includes a Sequence Listing.

SKIN CARE COMPOSITIONS CONTAINING PEPTIDE COMPOUND AND APHANOTHECE SACRUM EXOPOLYSACCHARIDE EXTRACT

FIELD OF THE INVENTION

The present invention is directed to the field of skin care compositions comprising a peptide compound.

BACKGROUND OF THE INVENTION

Certain peptides are reported to have skin care benefits such as anti-wrinkling. However, the efficacy of skin actives following topical application is determined, at least in part, by their bioavailability or the ability to reach their site of action within the skin. The outermost layer of skin, the stratum corneum, is made up of keratin-filled, non-viable cells embedded in a crystalline intercellular lipid domain and may impede delivery of compounds having a molecular weight close to or more than 500 Da. It is thus a challenge for skin actives such as peptides that have molecular weight more than 400 Da to cross the skin permeability barrier following topical application. Therefore, there is a need to improve skin active peptides delivery through the skin permeability barrier following topical application, and preferably in a cost-effective manner.

SUMMARY OF THE INVENTION

The inventors of the present invention surprisingly found that *Aphanothece sacrum* exopolysaccharide extract may be able to significantly increase skin active peptides (e.g. palmitoyl-KT and PKEK [SEQ ID NO: 2]) penetration through the skin permeability barrier following topical application. *Aphanothece sacrum* is a freshwater cyanobacteria. Examples of such extracts include those under the trademark SACRAN™ from Daito Kasei Koygyo Co., Ltd., Osaka City, Japan. Accordingly, one aspect of the invention provides a skin care composition, comprising: a peptide compound; and *Aphanothece sacrum* exopolysaccharide extract. Another aspect of the invention provides a method of beautifying skin comprising the step of applying the aforementioned skin care composition.

DETAILED DESCRIPTION OF THE INVENTION

Sequence Listing

A sequence listing that sets forth the amino acid sequences for SEQ ID NO: 1 to 17, which are primary sequences and include conservatively modified variants thereof, is being filed concurrently with the present application as an ASCII text file titled "AA1325_seq_list_ST25". This ASCII text file was created on Nov. 24, 2021 and is about 4 KB in size. In accordance with MPEP § 605.08 and 37 CFR § 1.52(e), the subject matter in the ASCII text file is incorporated herein by reference.

I. Compositions

The present invention relates to various compositions and, more specifically, to compositions for application to a skin surface including a wide variety of cosmetic, compositions. The compositions may be in various product forms that include, but are not limited to, solutions, suspensions, lotions, creams, gels, toilers, sticks, pencil, sprays, aerosols, ointments, cleansing liquid washes and solid bars, Shampoos and hair conditioners, pastes, foams, powders, mousses, shaving creams, wipes, strips, patches, electrically-powered patches, wound dressing and adhesive bandages, hydrogels, Pilin-forming products, facial and skin masks (with and without insoluble sheet), make-up such as foundations, eye liners, and eye shadows, and the like. The composition form may follow from the particular dermatologically acceptable carrier chosen, if present in the composition

II. *Aphanothece sacrum* exopolysaccharide extract

The skin care compositions comprise a *Aphanothece sacrum* exopolysaccharide extract. *Aphanothece sacrum* exopolysaccharide, of the *Aphanothece sacrum* exopolysaccharide extract, is a molecule with a relatively large molecular weight from about 16 million to about 20 million Daltons. The *Aphanothece sacrum* exopolysaccharide extract can be obtained through extraction techniques (e.g., solvents, pH, etc.) of biomaterial of *Aphanothece sacrum* known in the art. In one example, the extract is obtained by the alkaline dissolution of acid-washed biomaterial of *Aphanothece sacrum*. See e.g., Ngatu, N. R. et al (2012). Ann. Allergy Asthma Immunol., 108(2): 117-22. The extract is commercially available under the tradename SACRAN™. The exopolysaccharide of the extract is an anionic polysaccharide, with about 11 weight percent ("wt %") of sulfate groups and about 12 wt % of carboxyl groups per sugar chain. It is reported that the exopolysaccharide of the extract has more than ten types of monosaccharides contained therein including, but not limited, glucose, galactose, xylose, and fucose moieties. Sulfated muramic acid is a unique monosaccharide contained in the exopolysaccharide of the extract.

In one example, the *Aphanothece sacrum* exopolysaccharide of the extract has one, preferably at least two, more preferably at least three, yet still more preferably four of the following properties: (i) a molecular weight from 15 million Daltons (Da) to 25 million Da, preferably from 16-20 million Da; (ii) comprising from 5% to 20%, preferably 8% to 14%, more preferably from 9% to 12%, of sulfate groups, by weight of the exopolysaccharide; from 5% to 20%, preferably from 9% to 15%, more preferably from 11% to 13%, of carboxyl groups, by weight of the exopolysaccharide; (iii) comprising at least a muramic acid residue, preferably a sulfonated muramic acid residue; and/or (iv) comprising at least 7, preferably at least 9, more preferably at least 10, different monosaccharide moieties.

The skin care composition may comprise from comprises from 0.1% to 30%, preferably 1% to 20%, more preferably from 5% to 15%, yet more preferably from 8% to 12%, of the *Aphanothece sacrum* exopolysaccharide by weight of the skin care composition.

III. Peptide Compound

The skin care compositions comprise a peptide compound. "Peptide compound" is a compound having short amino acid chains (e.g., 2-50 amino acids). The peptide compound, for example, may comprise at least 2 amino acids, or 2 to 8 amino acids, or from 2 to 6 amino acids. In one non-limiting example, the peptide compound comprises a molecular weight greater than 400 Daltons (Da), or greater than 500 Da, or from 400 Da to 1,000 Da. Many peptide compounds are suitable for use in the skin care composition herein. For example, Pal-KT, a palmitoylated dipeptide, (palmitoyl-lysine-threonine) may have antiaging benefits. Palmitoyl-KTTKS [SEQ ID NO: 1] pentapeptide may help to improve the appearance of fine lines and wrinkles in aging facial skin. The tetrapeptide "PKEK" (Proline-Lysine-Glycine-Lysine), is reported to exert skin spot reduction and/or skin tone improvement. Additional, non-limiting examples of peptide compounds, that may have efficacy on human skin, are described.

One example of a type of peptide compound is matricin peptides. Specific examples may include Carnosine, Copper tripeptide, Trifluoroacetyl-tripeptide-2, Tripeptide-10 citrulline, Acetyl tetrapeptide-5 [SEQ ID NO: 3], Acetyl tetrapeptide-9 [SEQ ID NO: 4], Acetyl tetrapeptide-11 [SEQ ID NO: 5], Tetrapeptide PKEK [SEQ ID NO: 2], Tetrapeptide-21 [SEQ ID NO: 6], Hexapeptide, Hexapeptide-11 [SEQ ID NO: 7], Palmitoyl pentapeptide-4 [SEQ ID NO: 8], Palmitoyl tripeptide-3/5, Palmitoyl tetrapeptide-7 [SEQ ID NO: 9], Palmitoyl hexapeptide-12 [SEQ ID NO: 10], Palmitoyl oligopeptide, Palmitoyl tripeptide-1, and Pentamide-6.

Another example of a type of peptide compound is carrier peptides. Specific examples may include Copper tripeptide, Manganese tripeptide-1.

Another example of a type of peptide compound is peptide mimetics or neurotransmitter-inhibiting peptides. Specific examples may include Acetyl hexapeptide-3 [SEQ ID NO: 11], Pentapeptide-18 [SEQ ID NO: 12], Pentapeptide-3 [SEQ ID NO: 13], Tripeptide-3.

Another example of a type of peptide compound is enzyme inhibitor peptides. Specific examples may include Soybean peptide, Silk fibroin peptide, Black rice oligopeptides.

Another example of a type of peptide compound is structural protein digestion. A specific example may include Keratin peptide.

In another example, the peptide compound is selected from the group consisting of palmitoyl dipeptide, tetrapeptide, palmitoyl pentapeptide, acetyl hexapeptide, and combinations thereof.

In another example, the peptide compound is selected from the group consisting of palmitoyl-KT, PKEK [SEQ ID NO: 2], palmitoyl-KTTKS [SEQ ID NO: 1], acetyl hexapeptide-3 [SEQ ID NO: 11], acetyl hexapeptide-8 [SEQ ID NO: 16], and any combinations thereof.

Other non-limiting examples of peptides may include biologically active peptides under the trademark SYNTIDES® available from Psyclo Peptide, Inc. (Shanghai, China).

The skin care composition may comprise from 0.001% to 10%, preferably from 0.01% to 5%, more preferably from 0.1% to 2%, of the peptide compound by weight of the skin care composition.

IV. Skin Tone Agent.

Optionally, skin care composition may further comprise a skin tone agent in the composition. The skin tone agents can be included to further improve overall skin tone. When present, the compositions of the present invention contain up to 50%, 40%, 30%, 20%, 10%, 5%, or 3%, by weight of the composition, of the skin tone agent. When present, the compositions of the present invention contain at least 0.001%, 0.01%, 0.1%, 0.2%, 0.5%, or 1%, by weight of the composition, of the skin tone agent. Suitable ranges include any combination of the lower and upper limits including suitable ranges from 0.1% to 50%; from 0.2% to 20%; or from 1% to 10%, by weight of the composition, of the skin tone agent. Suitable skin tone agents include, but are not limited to, sugar amines, vitamin B3 compounds, arbutin, deoxyarbutin, 1,3-dihydroxy-4-alkylbenzene such as hexylresorcinol, sucrose dilaurante, bakuchoil (4-[(1E, 3S)-3-ethenyl-3,7-dimethyl-1,6 octadienyl] phenol or monterpene phenol), pyrenoine (available from Biotech Marine, France), *Panicum miliaceum* seed extract, arlatone dioic acid, cinnamic acid, ferulic acid, achromaxyl, methyl nicotinamide, oil soluble licorice extract, folic acid, undecylenic acid (i.e., undecenoic acid), zinc undecylenate, thiamine (Vitamin B1) and its hydrochloride, L-tryptophan, *Helianthus annuus* (sunflower) and *Vitis vinifera* (grape) leaf extract, carnosine (i.e., dragosine), methyl gentisate, 1,2-hexandiol and 1,2-octandiol (i.e., combination sold as Symdiol 68 by Symrise AG, Germany), inositol, decylenoylphenylalanine (e.g., sold under the tradename SEPIWHITE by Seppic, France), kojic acid, hexamidine compounds, salicylic acid, and retinoids including retinol and retinyl propionate, vitamin B3 compounds, sugar amines, hexamidine compounds, salicylic acid, 1,3-dihydroxy-4-alkylbenzene such as hexylresorcinol, and retinoids.

V. Anti-Inflammatory Agents

Optionally, the compositions may additionally comprise anti-inflammatory agents, which can be useful for improving the appearance of hyperpigmentation resulting from skin inflammation. Transient inflammatory events triggering hyperpigmentation and, more specifically, post-inflammatory hyperpigmentation include, but are not limited to, acne lesions, ingrown hairs, scratches, insect bites, surfactant damage, allergens, and short-term UV exposure. Inflammation induced hyperpigmentation including post-inflammatory hyperpigmentation may be managed by incorporating into the compositions of the present invention an anti-inflammatory agent. When present, the compositions of the present invention contain up to 20%, 10%, 5%, 3%, or 1% by weight of the composition, of the anti-inflammatory agent. When present, the compositions of the present invention contain at least 0.001%, 0.01%, 0.1%, 0.2%, 0.3%, 0.5%, or 1%, by weight of the composition, of the anti-inflammatory agent. Suitable ranges include any combination of the lower and upper limits. Suitable anti-inflammatory agents include, but are not limited to nonsteroidal anti-inflammatory agents (NSAIDS including but not limited to ibuprofen, naproxen, flufenamic acid, etofenamate, aspirin, mefenamic acid, meclofenamic acid, piroxicam and felbinac), glycyrrhizic acid (also known as glycyrrhizin, glycyrrhixinic acid, and glycyrrhetinic acid glycoside) and salts such as dipotassium glycyrrhizate, glycyrrhetenic acid, licorice extracts, bisabolol [e.g., alpha bisabolol), manjistha (extracted from plants in the genus *Rubia*, particularly *Rubia cordifolia*), and guggal (extracted from plants in the genus *Commiphora*, particularly *Commiphora mukul*), kola extract, chamomile, red clover extract, and sea whip extract (extracts from plant in the order Gorgonacea), derivatives of any of the foregoing, and mixtures thereof.

VI. Sunscreen Actives

Optionally, the compositions of the subject invention may further comprise one or more sunscreen actives (or sunscreen agents) and/or ultraviolet light absorbers. Herein, "sunscreen active" collectively includes, sunscreen actives, sunscreen agents, and/or ultraviolet light absorbers. Sunscreen actives include both sunscreen agents and physical sunblocks. Sunscreen actives may be organic or inorganic. Particularly suitable sunscreen actives are 2-ethylhexyl-pmethoxycinnamate (commercially available as PARSOL™ MCX), 4,4'-t-butyl methoxydibenzoyl-methane (commercially available as PARSOL™ 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5 trimethylcyclohexylsalicylate, menthyl anthranilate, p-dimethyl-aminobenzoic acid oraminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, benzylidene camphor and derivatives thereof, titanium dioxide, and mixtures thereof.

In an example, the composition may comprise from 1% to 20%, and alternatively, from 2% to 10% by weight of the composition, of the sunscreen active. Exact amounts will vary depending upon the chosen sunscreen active and the desired Sun Protection Factor (SPF), which is within the knowledge of one of skilled in the art.

VII. Dermatologically Acceptable Carrier

The compositions of the present invention may also comprise a dermatologically acceptable carrier (which may be referred to as "carrier") for the composition. The phrase "dermatologically acceptable carrier", as used herein, means that the carrier is suitable for topical application to the keratinous tissue, has good aesthetic properties, is compatible with the actives in the composition, and will not cause any unreasonable safety or toxicity concerns. In one embodiment, the carrier is present at a level of from 50% to 99%, 60% to 98%, 70% to 98%, or, alternatively, from 80% to 95%, by weight of the composition.

The carrier can be in a wide variety of forms. Non-limiting examples include simple solutions (e.g., aqueous, organic solvent, or oil based), emulsions, and solid forms (e.g., gels, sticks, flowable solids, or amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof.

The aqueous phase typically comprises water. However, in other embodiments, the aqueous phase may comprise components other than water, including but not limited to water-soluble moisturizing agents, conditioning agents, anti-microbials, humectants and/or other water-soluble skin care actives. In one embodiment, the non-water component of the composition comprises a humectant such as glycerin and/or other polyols. However, it should be recognized that the composition may be substantially (i.e, less than 1 wt % water) or fully anhydrous.

A suitable carrier is selected to yield a desired product form. Furthermore, the solubility or dispersibility of the components (e.g., extracts, sunscreen active, additional components) may dictate the form and character of the carrier. In one embodiment, an oil-in-water or water-in-oil emulsion is preferred.

Emulsions may further comprise an emulsifier. The composition may comprise any suitable percentage of emulsifier to sufficiently emulsify the carrier. Suitable weight ranges include from about 0.1% to about 10% or about 0.2% to about 5% of an emulsifier, based on the weight of the composition. Emulsifiers may be nonionic, anionic or cationic. Suitable emulsions may have a wide range of viscosities, depending on the desired product form. The carrier may further comprise a thickening agent as are well known in the art to provide compositions having a suitable viscosity and rheological character.

VIII. Methods of Treatment

Various methods of treatment, application, regulation, or improvement may utilize the aforementioned compositions. Identification of a region of aging skin may occur on any skin surface of the body. Skin surfaces of the most concern tend to be those not typically covered by clothing such as facial skin surfaces, hand and arm skin surfaces, foot and leg skin surfaces, and neck and chest skin surfaces (e.g., décolletage). In particular, identification of the region of aging skin may be on a facial skin surface including the forehead, periorial, chin, periorbital, nose, and/or cheek skin surfaces.

The method may comprise the step of applying the composition to the previously identified area of aging skin, or an area where one seeks to prevent the appearance of aging skin. Many regimens exist for the application of the composition. The composition may be applied at least once a day, twice a day, or on a more frequent daily basis, during a treatment period. When applied twice daily, the first and second applications are separated by at least 1 to about 12 hours. Typically, the composition may be applied in the morning and/or in the evening before bed.

The treatment period is ideally of sufficient time to provide an improvement in the appearance of aging skin. The treatment period may be at least about 1 week, and in some embodiments the treatment period may last about 4 weeks, 8 weeks, or 12 weeks. In certain embodiments, the treatment period will extend over multiple months (i.e., 3-12 months) or multiple years. In one embodiment the composition is applied at least once a day during a treatment period of at least about 4 weeks, 8 weeks, or 12 weeks. In one embodiment the composition is applied twice a day during a treatment period of at least about 4 weeks, 8 weeks, or 12 weeks.

The step of applying the composition may be accomplished by localized application. In reference to application of the composition, the terms "localized", "local", or "locally" mean that the composition is delivered to the targeted area (e.g., wrinkles around the eyes) while minimizing delivery to skin surface not requiring treatment. The composition may be applied and lightly massaged into area of aging skin. The form of the composition or the dermatologically acceptable carrier should be selected to facilitate localized application. While certain embodiments of the present invention contemplate applying a composition locally to an area, it will be appreciated that compositions of the present invention can be applied more generally or broadly to one or more skin surfaces. In some examples, the composition may be delivered by a variety of applicators appropriate for localized and general application. Such applicators can include droppers, applicator wands, cotton swabs, or any other suitable device. The applicator may be configured to easily apply the composition to signs of aging, such as fine lines and wrinkles, and allowing for a dosed amount of the composition of between 1 to 50 uL/cm$^2$ or between 1 to 5 uL/cm$^2$. In another example, the composition is applied to the one or more signs of aging and more generally to one or more facial skin surfaces contemporaneously (i.e., over a period of less than 30 minutes or, more typically, less than 5 minutes).

While some methods described herein contemplate applying the compositions of the present invention with an applicator, it will be appreciated that applicators are not required, and the compositions of the present invention can also be applied directly by using one's finger or in other conventional manners. One suitable method of improving the appearance of skin includes the step of topically applying a composition comprising effective amounts of a peptide compound and *Aphanothece sacrum* exopolysaccharide extract to the skin surface, wherein the composition is applied for a period of time sufficient to improve the appearance of the skin.

IX. Data

Data is provided to show that results of skin care formulation comprising 10 wt % SACRAN improve the skin penetration of peptide compound pal-KT and PKEK [SEQ ID NO: 2]. The method is described. The skin penetration of pal-KT (5 ppm) and PKEK [SEQ ID NO: 2] (40 ppm) is assessed using the Franz diffusion cell assay (4, T. J. Franz, *J. Invest. Dermatol.* 64: 190-195, 1975; T. J. Franz, et al., *Skin Pharmacol. Physiol.* 22: 276-286, 2009). The peptides are formulated in a skin care silicone-in-water (SWF) formulation with or without 10 wt % SACRAN. The formulations are spiked with $^{14}$C-pal-KT or $^{3}$H-PKEK. Twenty-four hours after topically dosed on human skin, residual product is removed from the skin surface, the epidermal and dermal layers were separated, and receptor solutions (transdermal) are collected. The SWF formulations are provided in Table 1 below:

TABLE 1

Examples of Skin Care Compositions (control and inventive) are provided.

| TRADE OR COMMON NAME | SWF + Pal-KT (Control) | SWF + Pal-KT + SACRAN | SWF + PKEK (Control) | SWF + PKEK + SACRAN |
|---|---|---|---|---|
| Silicone Phase | | | | |
| Cyclomethicone | 8.00 | 8.00 | 8.00 | 8.00 |
| Dimethicone 5 cst | 6.00 | 6.00 | 6.00 | 6.00 |
| DC-9045 Silicone Elastomer Blend | 4.00 | 4.00 | 4.00 | 4.00 |
| DC-9041 Silicone Elastomer Blend | 3.00 | 3.00 | 3.00 | 3.00 |
| DC Q2-1503 | 2.00 | 2.00 | 2.00 | 2.00 |
| DL-Alpha Tocopherol Acetate | 0.10 | 0.10 | 0.10 | 0.10 |
| Water Phase | | | | |
| Purified Water | qs | qs | qs | qs |
| Sacran | — | 0.1-20% | — | 0.1-20% |
| Glycerin | 7.00 | 7.00 | 7.00 | 7.00 |
| d-Panthenol | 0.50 | 0.50 | 0.50 | 0.50 |
| Glydant Plus Liquid | 0.30 | 0.30 | 0.30 | 0.30 |
| Disodium EDTA | 0.05 | 0.05 | 0.05 | 0.05 |
| Promatrixyl | — | 0.35 | — | 0.40 |
| Allantoin | 0.2 | 0.20 | 0.20 | 0.20 |
| Ultrez-21 | 0.20 | 0.2 | 0.2 | 0.2 |
| Sepigel 305 | 1.5 | 1.50 | 1.50 | 1.50 |
| Microthene FN510 | 1.00 | 1.00 | 1.00 | 1.00 |
| Total | 100.00 | 100.00 | 100.00 | 100.00 |

Results are described. As shown in Tables 2, pal-KT skin penetration is increased by the addition of SACRAN, showing statistical significance in epidermal and total (epidermis+dermis+receptor) penetration. There is also a statistically significant lower amount of pal-KT recovered from the surface of the skin that corresponded to the increase in total penetration.

Table 2. Penetration results of pal-KT in control and inventive compositions (described in Table 1) are provided.

TABLE 2

Effect of SACRAN on pal-KT Skin Penetration (ng/cm$^2$)

| | SWF | SWF + 10 wt % SACRAN |
|---|---|---|
| Surface Residual | 228.5 ± 10.2 | 173.2 ± 18.1 |
| Epidermis | 72.5 ± 9.5 | 128.3 ± 17.1 |
| Dermis | 14.3 ± 1.4 | 14.8 ± 1.65 |

TABLE 2-continued

Effect of SACRAN on pal-KT Skin Penetration (ng/cm$^2$)

| | SWF | SWF + 10 wt % SACRAN |
|---|---|---|
| Receptor | 0.14 ± 0.14 | 0.09 ± 0.07 |
| Total Penetration | 88.0 ± 10.2 | 143.3 ± 18.1 |

The ability of SACRAN to enhance PKEK [SEQ ID NO: 2] skin penetration is also assessed in Table 3. A numerical increase in PKEK [SEQ ID NO: 2] penetration is shown. Again, the decrease in residual peptide recovered from the surface of the skin corresponded with the increase in total penetration.

Table 3. Penetration results of PKEK [SEQ ID NO: 2] in control and inventive compositions (described in Table 1) are provided.

TABLE 3

Effect of SACRAN on PKEK Skin Penetration (ng/cm$^2$)

| | SWF | SWF + 10 wt % SACRAN |
|---|---|---|
| Surface Residual | 2048 ± 59 | 1762 ± 161 |
| Epidermis | 258 ± 31 | 382 ± 67 |
| Dermis | 54 ± 10 | 49 ± 11 |
| Receptor | 169 ± 54 | 339 ± 134 |
| Total Penetration | 483 ± 59 | 770 ± 161 |

The addition of the polysaccharide, SACRAN, to SWF produced a 60% increase in pal-KT and PKEK [SEQ ID NO: 2] skin penetration following a single topical application. Without wishing to be bound by theory, it is possible that SACRAN is acting as a film-former allowing for longer delivery times for the peptide compounds to partition out of the formula and into the skin.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of beautifying skin, comprising:
applying a skin care composition to a target portion skin in need of treatment, the skin care composition comprising:
one or more peptide compounds; wherein at least one peptide compound is selected from the group consisting of palmitoyl dipeptide, tetrapeptide, palmitoyl pentapeptide, acetyl hexapeptide, and combinations thereof; and
1% to 20% of *Aphanothece sacrum* exopolysaccharide extract by weight of the composition, wherein the amount of *Aphanothece sacrum* exopolysaccharide extract is sufficient to increase skin penetration of the peptide compound by at least 60% according to the Franz diffusion cell assay.

2. The method of claim 1, wherein the *Aphanothece sacrum* exopolysaccharide extract comprises an *Aphanothece sacrum* exopolysaccharide with a molecular weight of about 15 million Daltons (Da) to about 25 million Da.

3. The method of claim 2, wherein the *Aphanothece sacrum* exopolysaccharide comprises about 5% to about 20% of sulfate groups, by weight of the exopolysaccharide.

4. The method of claim 2, wherein the *Aphanothece sacrum* exopolysaccharide comprises about 9% to about 12% of sulfate groups, by weight of the exopolysaccharide.

5. The method of claim 2, wherein the *Aphanothece sacrum* exopolysaccharide comprises about 5% to about 20% of carboxyl groups, by weight of the exopolysaccharide.

6. The method of claim 5, wherein the *Aphanothece sacrum* exopolysaccharide comprises about 9% to about 15% of carboxyl groups, by weight of the exopolysaccharide.

7. The method of claim 6, wherein the *Aphanothece sacrum* exopolysaccharide comprises about 11% to about 13% of carboxyl groups, by weight of the exopolysaccharide.

8. The method of claim 2, wherein the *Aphanothece sacrum* exopolysaccharide comprises a muramic acid residue.

9. The method of claim 8, wherein the *Aphanothece sacrum* exopolysaccharide comprises a sulfonated muramic acid residue.

10. The method of claim 1, wherein the *Aphanothece sacrum* exopolysaccharide extract comprises an *Aphanothece sacrum* exopolysaccharide with at least 7 different monosaccharide moieties.

11. The method of claim 10, wherein the *Aphanothece sacrum* exopolysaccharide comprises at least 10 different monosaccharide moieties.

12. The method of claim 1, wherein the skin care composition comprises about 5% to about 5% *Aphanothece sacrum* exopolysaccharide by weight of the skin care composition.

13. The method of claim 1, wherein the peptide compound comprises at least 2 amino acids.

14. The method of claim 1, wherein the peptide compound has a molecular weight greater than 400 Da.

15. The method of claim 1, wherein the peptide compound is present at about 0.001% to about 10%, by weight of the skin care composition.

16. The method of claim 1, wherein the one or more peptide compounds is selected from the group consisting of palmitoyl-KT, PKEK [SEQ ID NO: 2], palmitoyl-KTTKS [SEQ ID NO: 1], acetyl hexapeptide-3, acetyl hexapeptide-8 [SEQ ID NO: 16], and combinations thereof.

17. The method of claim 1, wherein the one or more peptide compounds is selected from a matricin peptide, carrier peptide, peptide mimetic, neurotransmitter-inhibiting peptide, enzyme inhibitor peptide, and combinations thereof.

\* \* \* \* \*

SEQUENCE LISTING

<160> NUMBER OF SEQ ID NOS: 17

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Lys Thr Thr Lys Ser
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Pro Lys Glu Lys
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct

<400> SEQUENCE: 3

Ala His Ser His
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Construct

<400> SEQUENCE: 4

Gln Asp Val His
1

<210> SEQ ID NO 5
<211> LENGTH: 4
<212> TYPE: PRT
<213> ORGANISM: Artificial Sequence
<220> FEATURE:
<223> OTHER INFORMATION: Synthetic Construct

<400> SEQUENCE: 5

Pro Pro Tyr Leu
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Construct

<400> SEQUENCE: 6

Gly Glu Lys Gly
1

```
<210> SEQ ID NO 7
<211> LENGTH: 6
<212> TYPE: PRT
<213> ORGANISM: Artificial Sequence
<220> FEATURE:
<223> OTHER INFORMATION: Synthetic Construct

<400> SEQUENCE: 7

Phe Val Ala Pro Phe Pro
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct

<400> SEQUENCE: 8

Lys Thr Thr Lys Ser
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic Construct

<400> SEQUENCE: 9

Gly Gln Pro Arg
1

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

Val Gly Val Ala Pro Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Construct

<400> SEQUENCE: 11

Glu Met Gln Arg Arg
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Tyr Ala Gly Phe Leu
1               5
```

```
<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

<400> SEQUENCE: 13

Gly Pro Arg Pro Ala
1               5

<210> SEQ ID NO 14
<211> LENGTH: 4
<212> TYPE: PRT
<213> ORGANISM: Artificial Sequence
<220> FEATURE:
<223> OTHER INFORMATION: Synthetic Construct

<400> SEQUENCE: 14

Ala Arg Phe Asp
1

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct

<400> SEQUENCE: 15

Lys Thr Thr Lys Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct

<400> SEQUENCE: 16

Glu Glu Met Gln Arg Arg
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Glu Met Gln Arg Arg
1               5
```